United States Patent [19]

Tuttle et al.

[11] Patent Number: 4,774,230

[45] Date of Patent: Sep. 27, 1988

[54] GLUCURONIC ACID DERIVATIVES OF OPIOID ANTAGONISTS

[75] Inventors: Ronald R. Tuttle, Plantation; Ross Dixon, Boca Raton; Maciej M. Smulkowski, Gainesville, all of Fla.

[73] Assignee: Ivax Laboratories, Inc., Miami, Fla.

[21] Appl. No.: 844,417

[22] Filed: Mar. 26, 1988

[51] Int. Cl.⁴ .................. A61K 31/70; C07H 15/24
[52] U.S. Cl. .................................. 514/27; 536/4.1; 536/17.4; 536/18.1
[58] Field of Search ............... 546/44; 536/17.4, 18.1; 514/27

[56] References Cited

PUBLICATIONS

Fujimoto et al., Chemical Abstracts, vol. 71, 1969, p. 130, No. 37250y.
Fujimoto et al., Chemical Abstracts, vol. 72, 1970, p. 131, No. 98055f.

*Primary Examiner*—J. R. Brown
*Assistant Examiner*—Elli Peselev
*Attorney, Agent, or Firm*—Kirschstein, Kirschstein, Ottinger & Israel

[57] ABSTRACT

Intestine-specific delivery of an opioid antagonist can be accomplished without substantial central nervous system effects by administering the antagonist orally in the form of the glucuronide derivative.

9 Claims, 2 Drawing Sheets

GLUCURONIC ACID DERIVATIVES OF OPIOID ANTAGONISTS

BACKGROUND OF THE INVENTION

This invention relates to glucuronic acid derivatives of opioid antagonists, and more particularly to the therapeutic use of such compounds in the treatment of localized symptoms with a minimum of systemic effects.

Opioid antagonists are a well-known class of drugs which can be used to prevent or promptly reverse the effects of morphine-like opioid agonists. See *Goodman and Gilman's The Pharmacological Basis of Therapeutics*, Sixth Edition, pp. 521-525. It is known that the opioid antagonist, naloxone, is converted by the human body to the glucuronide form, although no use for this form of naloxone has been found before the present invention. Of particular interest among the known opioid antagonists is nalmefene, which was first identified and claimed in U.S. Pat. No. 3,814,768 as 6-methylene-6-desoxy-N-cyclopropylmethyl-14-hydroxydihydronormorphine.

The constipating effect of opioids is the oldest known effect of these drugs. Indeed constipation is the most troubling side effect when opioid drugs are employed to relieve pain. Patients who require opioid analgesics to relieve pain on a chronic basis e.g. cancer victims, suffer severe constipation. Such constipation is also common among opioid addicts, and may even be a problem for those being given opioids on a short term basis, such as patients undergoing surgery.

Sudden withdrawal of opioid drugs following prolonged exposure provokes intestinal hypermotility and diarrhea results. This withdrawal phenomenon of hypermotility and diarrhea is also produced if an opioid antagonist is given after prolonged opioid administration. Thus the opioid can cause hypomotility and constipation, and withdrawal can cause the opposite effect of hypermotility and diarrhea. Hypomotility and hypermotility are dysmotilities at the extreme ends of the spectrum of intestinal motility. If an opioid antagonist were administered throughout the period of opioid exposure, intestinal dysmotility at both ends of the spectrum could be forestalled.

Attempts have been made to provide opioid antagonists that would relieve the constipating effect of exogenous opioids without antagonizing the analgesic effect. This is particularly important for chronic users or addicts since systemic antagonism can cause severe withdrawal symptoms mediated by the central nervous system. One class of compounds which has been investigated for this purpose are the quaternary ammonium derivatives of known narcotic antagonists (U.S. Pat. No. 4,176,187). The quaternary antagonists antagonize opioid induced intestinal hypomotility at lower doses than are required to antagonize opioid induced analgesia. The selective antagonism, i.e. more effective on intestinal hypomotility than on central nervous system analgesia, occurs because quaternary compounds are highly charged. The blood brain barrier impedes passage of highly charged drugs. Thus, the quaternary ammonium antagonists have more limited access to the opioid receptors in the central nervous system (CNS) that mediate analgesia than they do to the opioid receptors in the intestine that mediate hypomotility.

It is doubtful however that the quaternary ammonium antagonists will provide a practical solution to the clinical problem of the constipating effects of opioid analgesics. It has been known since the work of Eddy in 1933 (J. Pharmacol. Exp. Therap., 1967, 157: 185-195) that "quaternarization" was a means of directing opioids away from the CNS and toward the intestine. Yet no clinically useful quaternary opioid antagonist is available to patients. The failure of such a drug to emerge in therapeutics is likely related to the toxic effects on the autonomic nervous system that are known to occur with quaternary ammonium drugs.

In addition to relieving the constipating effects of exogenous opioids, the present invention is also directed to preventing endogenous opioids from exacerbating intestinal dysmotility of irritable bowel syndrome. In the last decade it's been discovered that the body produces its own opioids. The endogenous opioids are called endorphins and enkephalins. There is an abundance of endogenous opioids and opioid receptors in the intestinal tract. From the work of Kreek et al. (Lancet 1983 1: 262) it appears that such endogenous opioids contribute to intestinal dysmotility. Kreek et al. have shown that the opioid antagonist naloxone relieves constipation even though the patients have not been exposed to an exogenous opioid.

Irritable bowel syndrome is a form of intestinal dysmotility well known to gastroenterologists. The syndrome is characterized by pain as well as alternating constipation and diarrhea. The endogenous opioids may exacerbate the syndrome. The hypomotility and constipation phase of the syndrome could be the result of an excessive endogenous opioid influence, while the hypermotility and diarrhea could result from an abrupt cessation of endogenous opioid activity. In irritable bowel syndrome we believe that there is an exaggerated cyclic effect of the endogenous opioids on the intestines. During the upphase of the cycle the intestines can be immobilized and become physically dependent upon the endogenous opioids. During the down phase of the cycle the intestines can go into withdrawal, and thus become hypermotile and produce diarrhea. Pain can result from both constipation and diarrhea.

It appears then that a cycling auto-addiction and withdrawal is an important contributor to irritable bowel syndrome. Just as the continued presence of an opioid antagonist would prevent the addiction or physical dependence of the intestines to exogenous opioids, an antagonist should similarly prevent the exacerbating influence of cycling endogenous opioids on the intestine.

SUMMARY OF THE INVENTION

It is therefore an object of the present invention to provide an opioid antagonist which has a local therapeutic effect in the intestinal tract with a minimum of systemic effects, particularly central nervous system (CNS) effects.

A further object of this invention is to provide chemical analogs of known opioid antagonists which have a local intestinal effect with little or no CNS effects.

A still further object of this invention is to provide a method for treating intestinal dysmotility by administration of an opioid antagonist which has a minimum of CNS effects.

In accordance with the above objects of this invention, glucuronic acid derivatives of opioid antagonists are provided for the treatment of intestinal dysmotility with a minimum of systemic effects. Nalmefene glucuronide has been found particularly useful for achieving the objects of this invention.

DETAILED DESCRIPTION

Figure 1:
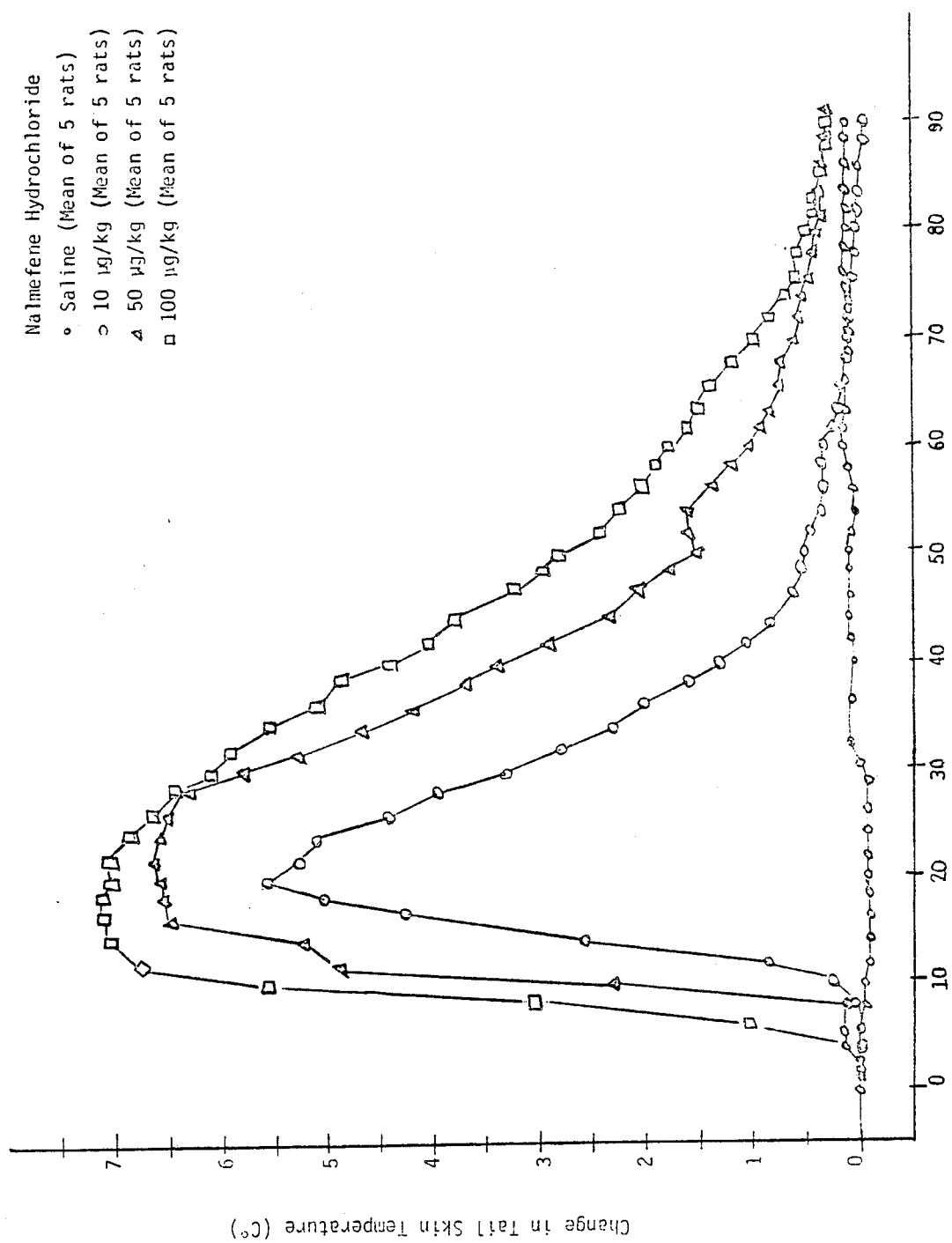

This invention uses the β-D-glucuronic acid derivatives of opioid antagonists for colon specific drug delivery. These compounds are given by the following general formula:

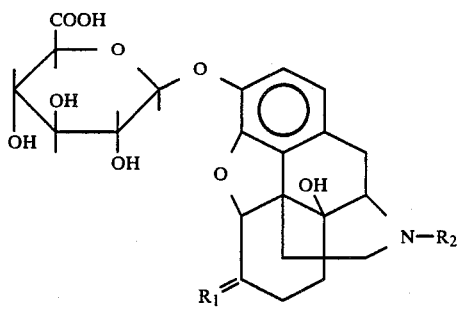

wherein $R_1$ is either =O or =$CH_2$, and $R_2$ is allyl or cyclopropylmethyl. Three compounds of particular interest are nalmefene-3β-D-glucuronide ($R_1$ is =$CH_2$ and $R_2$ is cyclopropylmethyl), naloxone-3β-D-glucuronide ($R_1$ is =O and $R_2$ is allyl) and naltrexone-3β-D-glucuronide ($R_1$ is =O and $R_2$ is cyclopropylmethyl).

In accordance with the present invention, it has been found that these glucuronide compounds have little or no opioid antagonistic effect unless they are enzymatically cleaved to yield the free antagonist. For example:

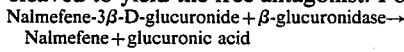

β-glucuronidase is a naturally occuring enzyme which is present in the bacterial flora of the lower intestinal tract, particularly in the colon. Therefore the compounds of this invention provide a means of specific delivery of an opioid antagnoist to the lower intestinal tract. Opioid antagonist activity in the body outside the intestine is avoided because glucuronic acid derivatives are poorly absorbed and rapidly eliminated in the urine. Further, the glucuronides do not encounter β-glucuronidase outside the intestine.

After liberation of the aglycone antagonist in the lower intestinal tract, small amounts of this aglycone antagonist could be absorbed into the portal circulation. However as the aglycone antagonist passes into the portal blood and through the liver it will be reconverted to its β-D-glucuronide conjugate by hepatic glucuronyl transferase. Therefore no significant amount of active antagonist will reach the systemic circulation.

An analysis of the blood and urine of rats treated with nalmefene orally showed that the concentration of nalmefene glucuronide is about 100 fold higher than is the concentration of free nalmefene. Thus nalmefene is almost totally biotransformed as a result of "first-pass" metabolism when administered orally. Such a high degree of biotransformation is common for this type of drug. However it was discovered that the relative concentrations of free nalmefene and nalmefene glucuronide in the feces of these animals were in marked contrast to the blood and urine. Whereas the ratio of nalmefene to nalmefene glucuronide in the blood and urine was about 1:100, in the feces the ratio was about 3:1. This suggests that some of the nalmefene glucuronide formed from nalmefene as a result of "first-pass" metabolism in the liver, was excreted via the bile into the intestine and subsequently hydrolysed by intestinal micro flora to yield free nalmefene.

This observation led to developing opioid antagonist drugs with activity confined to the intestine. This intestinal specificity would provide for the following three therapeutic applications:

(1) Preventing the unwanted constipation (side effect) caused by opioid analgesic drugs without interfering with the wanted analgesic effect.
(2) Treating idiopathic constipation.
(3) Treating irritable bowel syndrome.

SYNTHESIS

The compounds according to the present invention can be prepared by the reaction of opioid antagonists salts (for example lithium salts) with the appropriate bromosugar followed by alkaline hydrolysis of the protecting groups. These compounds can also be obtained by the Koenigs-Knorr reaction (R. L. Whistler and M. L. Wolfrom, "Methods in Carbohydrate Chemistry"; R. B. Conrow and S. Bernstein, J. Org. Chem. 1971, (36), 863 and literature cited therein) followed by alkaline hydrolysis.

The present invention is described in more detail by way of the following non-limiting examples. Examples 1 and 2 are synthesis of precursor materials and are described in Bollenback, et al., J. Am. Chem. Soc. 1955, (77), 3310.

EXAMPLE 1

40 g of D-glucurono-6,3-lactone was added to a solution of 0.11 g of sodium hydroxide in 300 ml of methanol. The mixture was stirred at room temperature for 1 hour and the methanol was then removed under vacuum. The residue was dissolved in 100 ml of pyridine and 150 ml of acetic anhydride was added at 0 C. After 18 hours at 0 C. the precipitate was filtered and recrystallized from ethanol. 38 g of methyl tetra-O-acetyl-β-D-glucopyranuronate was obtained, with M.P. 176.5–178 C.; $[\alpha]_D^{22}$ = +7.668 (c 1, $CHCl_3$).

EXAMPLE 2

5 g of methyl tetra-O-acetyl-β-D-glucopyranuronate was dissolved in 20 ml of 30% hydrobromic acid in acetic acid and the reaction mixture was kept overnight at 0 C. The solvent was then removed under vacuum and the residue was dissolved in 25 ml of chloroform. This solution was extracted with cold aqueous sodium bicarbonate and water, dried over sodium sulfate and the solvent was removed under vacuum. The residual syrup was crystallised from ethanol and 4.5 g of methyl(tri-O-acetyl-α-D-glucopyranosyl bromide)-uronate was obtained with M.P. 105–7 C., $[\alpha]_D^{25}$ = +196.2 (c 1, $CHCl_3$).

EXAMPLE 3

To a solution of 2.555 g of nalmefene free base and 0.269 g of lithium hydroxide monohydrate in 11 ml of methanol was added 2.15 g of methyl (tri-O-acetyl-α-D-glucopyranosyl bromide)-uronate. After 30 min at room temperature a solution of 0.430 g of lithium hydroxide in 11 ml of water was added. After another 30 min the reaction was brought to pH 8 with acetic acid and the unreacted nalmefene was filtered off. The filtrate was evaporated and the residual syrup was chromatographed on a silica gel column with chloroform:methanol = 3:2 as elutant. It was then further purified on an H+ form ion-exchange resin with ammonium hydroxide solution as elutant and 0.78 g of nalmefene-3β-D-glucuronide was obtained.

| Elemental analysis | C | H | N |
|---|---|---|---|
| Calculated for $C_{27}H_{33}NO_9 \cdot 2H_2O$ | 58.79 | 6.76 | 2.54 |
| Found | 58.76 | 6.78 | 2.53 |

EXAMPLE 4

A solution of 0.397 g of methyl(tri-O-acetyl-α-D-glucopyranosyl bromide)-uronate in 10 ml of toluene was added dropwise over a period of 1 hour to a mixture of 0.17 g of nalmefene free base and 0.172 g of cadmium carbonate in 10 ml of toluene. During the addition, 10 ml of toluene was also removed from the reaction mixture by distillation. Distillation of toluene was continued for another 0.5 hour during which time an equal volume of toluene was added dropwise to the reaction mixture. The inorganic salts were then removed by filtration and the filtrate was evaporated. The residue was chromatographed on a silica gel column with chloroform:methanol=9:1 as elutant. This gave 0.240 g of methyl (nalmefene-tri-O-acetyl-β-D-glucopyranosid)-uronate.

EXAMPLE 5

To the solution of 0.830 g of nalmefene free base and 0.087 g of lithium hydroxide monhydrate in 4 ml of methanol was added 0.7 g of methyl(tri-O-acetyl-α-D-glucopyranosyl bromide)-uronate. After 30 min at room temperature the reaction mixture was brought to pH 8 with acetic acid and the unreacted nalmefene was filtered off. The filtrate was evaporated and the residual syrup was chromatographed on a silica gel column with chloroform:methanol=9:1 as elutant. 0.81 g of methyl(-nalmefene-tri-O-acetyl-β-D-glucopyranosid)-uronate was obtained.

EXAMPLE 6

To a solution of 0.81 g of methyl(nalmefene-tri-O-acetyl-β-D-glucopyranosid)uronate in 3.6 ml of methanol was added a solution of 0.12 g of lithium hydroxide in 3.6 ml of water. After 30 min at room temperature the reaction mixture was brought to pH 8 with acetic acid and the solvents were removed under vacuum. The residual syrup was purified as in example 3 and 0.41 g of nalmefene-3β-D-glucuronide was obtained. This was identical to the product in example 3.

EXAMPLE 7

To a solution of 3.7 g of naloxone free base and 0.4 g of lithium hydroxide in 16 ml of water was added 3.26 g of methyl(tri-O-acetyl-β-D-glucopyranosyl bromide)-uronate. After 30 min at room temperature a solution of 0.65 g of lithium hydroxide in 16 ml of water was added. After another 30 min the reaction was brought to pH 8 with acetic acid and the unreacted naloxone was filtered off. The filtrate was evaporated and the residual syrup was crystallized from 95% ethanol and 2.27 g of naloxone-3β-D-glucuronide was obtained.

| Elemental analysis | C | H | N |
|---|---|---|---|
| Calculated for $C_{25}H_{29}NO_{10} \cdot 2H_2O$ | 55.65 | 6.16 | 2.6 |
| Found | 55.27 | 5.86 | 2.54 |

TEST RESULTS

To determine whether nalmefene glucuronide would alleviate morphine-induced hypomotility, the charcoal meal assay method of Witkin et al. (J. Pharmacol. Ext. Therep., 133: 400, 1961) was done on 56 mice. The results of the assay are given in Table 1 below. These results show that nalmefene-β-D-glucuronide was as effective as nalmefene in alleviating the depressant effects of morphine on intestinal transit.

TABLE 1

Summary of the Results of the Charcoal Meal Assay[a] (Gastrointestial Motility) in Mice Given Nalmefene HCl and Nalmefene-β-D-Glucuronide

| Group | Treatment[b] | Percent Meal Traveled ± S.E.M. (N) = # of Mice |
|---|---|---|
| 1 | Saline + Saline | 68 ± 2 (N = 14) |
| 2 | Saline + Morphine | 28 ± 2 (N = 8)[c] |
| 3 | Morphine + Saline | 31 ± 3 (N = 8)[c,g] |
| 4 | Saline + Nalmefene Glucuronide | 66 ± 3 (N = 8)[d] |
| 5 | Morphine + Nalmefene Glucuronide | 58 ± 12 (N = 5)[d,e,h,i] |
| 6 | Saline + Nalmefene HCl | 63 ± 2 (N = 8)[c] |
| 7 | Morphine + Nalmefene HCl | 66 ± 14 (N = 5)[d,e,f] |

[a] Witkin et al., JPET 133: 400, 1961.
[b] The first vehicle or drug listed under Treatment was given 30 minutes before the second vehicle or drug listed. The results were determined 30 min later. All treatments are p.o. and given in a volume of 0.3 ml. Doses were 10 mg/kg for morphine, 15 mg/kg or 2.9 × 10⁻⁶ M/kg for nalmefene glucuronide and 2.9 × 10⁻⁶ M/kg for nalmefene HCl.
[c] Significantly different (p < 0.05) from Saline + Saline controls.
[d] No significant difference compared with Saline + Saline group.
[e] Significantly different (p < 0.05) from Morphine + Saline group.
[f] No significant difference compared with Saline + Nalmefene group.
[g] No significant difference compared with Saline + Morphine group.
[h] No significant difference compared with Saline + Nalmefene Glucuronide.
[i] No significant difference compared with Morphine + Nalmefene group.

Group 1 shows that the percentage of the intestinal tract traveled by the charcoal meal when no drug is given (just vehicle control) is 69±2%. Morphine (groups 2 and 3) reduced the percentage of the intestine traveled by more than half.

In the absence of morphine neither nalmefene (group 6) nor nalmefene glucuronide (group 4) had any significant effect. However both nalmefene (group 7) and nalmefene glucuronide (group 5) protected the intestine against the depressant effect of morphine. In these latter two groups the percentage of intestine traveled was not significantly less than in the group (group 1) where no morphine was present.

Having found that nalmefene-3β-D-glucuronide was as effective as nalmefene in preventing morphine-induced intestinal hypomotility, experiments were done to determine whether nalmefene-glucuronide lacked opioid antagonist effect in the central nervous system.

The Rapid Quantitative In Vivo Assay for Narcotic Antagonist of Katovich et al. (Substance and Alcohol Actions/Misuse, vol 5: 87095, 1984) was used. This assay is based on the extreme sensitivity of opioid-dependant animals to narcotic antagonists. Injection of these animals with a narcotic antagonist produces severe central nervous system withdrawal signs. One of these signs is an abrupt rise in the skin temperature of the tail.

Figure 2:
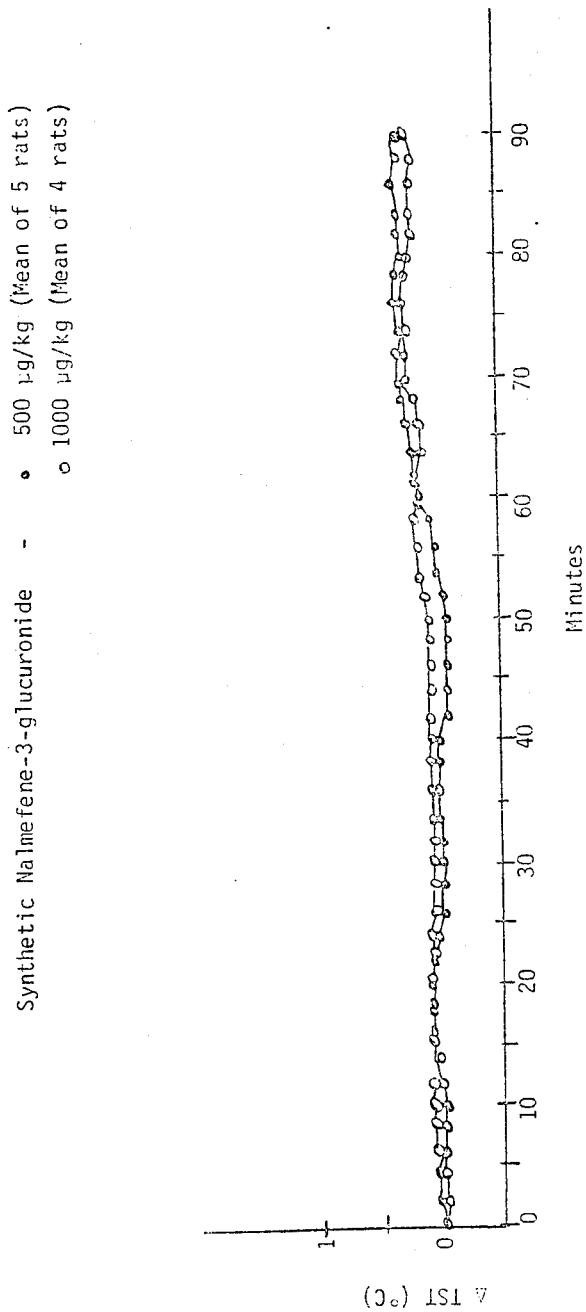

FIG. 1 shows the marked rise in skin tail temperature in response to nalmefene in doses as low as 10 μg/kg. Yet, as FIG. 2 shows, an injection of 1000 μg/kg of nalmefene glucuronide had no effect. Additional studies in rats using $^{14}C$ labelled nalmefene glucuronide demonstrated that nalmefene glucuronide is not absorbed to any measurable extent following oral administration of doses as high as 40 mg/kg. No radioactivity could be detected in plasma 2 hours after dosing while about 85% of the dose was present in the small intestine still as nalmefene glucuronide. However the 2-3% of the dose which had reached the cecum by this time was almost exclusively free nalmefene. Therefore the glucuronide of an opioid antagonist provides a means of preventing narcotic-induced intestinal hypomotility without interfering with central nervous system effects of narcotics, such as analgesia.

The glucuronide derivatives should be administered orally, preferably in the form of capsules or tablets. Known coating and tabletting agents can be used. As examples, known enteric coatings like polyacrylates and cellulose acetate phthalates may be used as coatings for the active ingredient. The amount of glucuronide derivative administered at one time is from about 0.1 to 50 mg, preferably 0.5-20 mg.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

We claim:
1. A compound of formula:

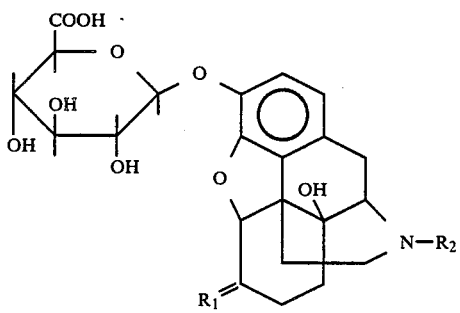

wherein $R_1$ is $=CH_2$ or $=O$ and $R_2$ is cyclopropylmethyl.

2. A compound according to claim 1, wherein $R_1$ is $=O$ and $R_2$ is cyclopropylmethyl.

3. A composition for site-specific delivery of an opioid antagonist to the intestine of a subject without substantial systemic effects, comprising nalmefene-3β-D-glucuronide or naltrexone-3β-D-glucuronide in an amount sufficient to provide opioid antagonism to the intestine of the subject and a pharmaceutically acceptable carrier for oral administration.

4. A method for providing site specific opioid antagonism in the intestine of a subject without substantial systemic effects, comprising orally administering to said subject an amount of an opioid antagonist sufficient to provide opioid antagonism to the intestine of a subject in the form of a glucuronide derivative having the formula:

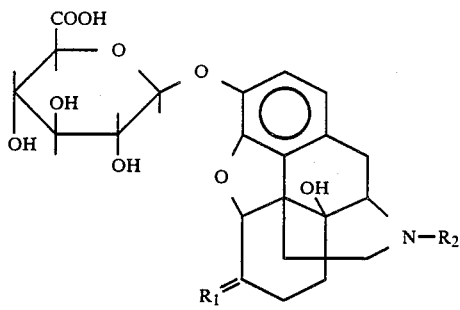

wherein $R_1$ is $=O$ or $=CH_2$ and $R_2$ is allyl or cyclopropylmethyl.

5. The method of claim 4, wherein the glucuronide derivative is selected from
nalmefene-3β-D-glucuronide,
naloxone-3β-D-glucuronide and
naltrexone-3β-D-glucuronide.

6. The method of claim 5, wherein the glucuronide derivative is nalmefene-3β-D-glucuronide.

7. A method of treating intestinal dysmotility in a subject suffering from an intestinal dysmotility, without substantial systemic effects, comprising orally administering to the subject an opioid antagonist in the form of a glucuronide derivative, having the formula:

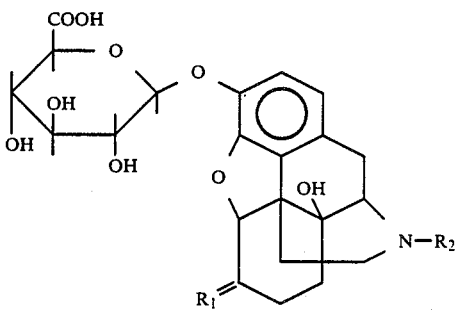

wherein $R_1$ is $=O$ or $=CH_2$ and $R_2$ is allyl or cyclopropylmethyl, the amount of said glucuronide derivative being sufficient to provide opioid antagonism in the intestine of the subject, the glucuronide derivative undergoing cleavage in the intestine of the subject to assume the aglycone form of the antagonist.

8. The method of claim 7, wherein the glucuronide derivative is selected from
nalmefene-3β-D-glucuronide,
naloxone-3β-D-glucuronide and
naltrexone-3β-D-glucuronide.

9. The method of claim 8, wherein the glucuronide derivative is nalmefene-3β-D-glucuronide.

* * * * *

Disclaimer 4,774,230.—*Ronald R. Tuttle*, Plantation; *Ross Dixon*, Boca Raton; *Maciej M. Smulkowski*, Gainesville, all of Fla. GLUCURONIC ACID DERIVATIVES OF OPIOID ANTAGONISTS. Patent dated Sept. 27, 1988. Disclaimer filed June 22, 1989, by the assignee, Baker Cummins Pharmaceuticals, Inc.

Hereby enters this disclaimer to claims 1 and 2 of said patent.
[*Official Gazette November 21, 1989*]